United States Patent
Thiele (10) Patent No.: US 9,123,101 B2
(45) Date of Patent: Sep. 1, 2015

(54) AUTOMATIC QUANTIFICATION OF ASYMMETRY

(75) Inventor: Frank Olaf Thiele, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 77 days.

(21) Appl. No.: 13/977,025

(22) PCT Filed: Jan. 3, 2012

(86) PCT No.: PCT/IB2012/050025
§ 371 (c)(1),
(2), (4) Date: Jun. 28, 2013

(87) PCT Pub. No.: WO2012/093353
PCT Pub. Date: Jul. 12, 2012

(65) Prior Publication Data
US 2013/0289395 A1    Oct. 31, 2013

Related U.S. Application Data

(60) Provisional application No. 61/429,777, filed on Jan. 5, 2011.

(51) Int. Cl.
G06K 9/00  (2006.01)
G06T 7/00  (2006.01)
G06T 7/60  (2006.01)
A61B 5/00  (2006.01)

(52) U.S. Cl.
CPC ............. *G06T 7/0014* (2013.01); *A61B 5/0042* (2013.01); *G06T 7/608* (2013.01); *G06T 2207/10104* (2013.01); *G06T 2207/30016* (2013.01)

(58) Field of Classification Search
None
See application file for complete search history.

(56) References Cited

U.S. PATENT DOCUMENTS

| 7,471,812 | B2 * | 12/2008 | Cho et al. | 382/125 |
| 8,218,835 | B2 * | 7/2012 | Matsuda et al. | 382/128 |
| 8,498,481 | B2 * | 7/2013 | Blake et al. | 382/173 |
| 8,838,204 | B2 * | 9/2014 | Edelman et al. | 600/413 |
| 8,849,000 | B2 * | 9/2014 | Hu | 382/131 |

(Continued)

FOREIGN PATENT DOCUMENTS

JP  2008026144 A  2/2008
RU  2356498 C1  5/2009

OTHER PUBLICATIONS

Aubert-Broche, B., et al.; Evaluation of Methods to Detect Interhemispheric Asymmetry on Cerebral Perfusion SPECT: Application to Epilepsy; 2005; J. Nucl. Med.; 46:707-713.

(Continued)

*Primary Examiner* — Nancy Bitar (57) ABSTRACT

An apparatus detects asymmetry in an object, such as a brain. The apparatus includes a processor programmed to fit a three-dimensional image of the object to a preselected shape, such as a standard brain atlas. The processor projects the three-dimensional image of the object to a two-dimensional surface image. The processor compares corresponding mirror image symmetric voxel pairs on the left and right sides of the surface image. The processor generates at least one of an asymmetry map and an asymmetry index based on the deviations in the pixel pairs. The processor can also mask, before the comparison, pixels of the surface image which are asymmetric in a normal brain.

17 Claims, 6 Drawing Sheets

(56) References Cited

U.S. PATENT DOCUMENTS

2008/0021502 A1* 1/2008 Imielinska et al. ............ 607/1
2008/0292194 A1* 11/2008 Schmidt et al. ............ 382/217

OTHER PUBLICATIONS

Chen, Z., et al.; Pathological Lesion Detection in 3D Dynamic PET Images Using Asymmetry; 2003; IEEE trans. on Image Analysis and Processing; pp. 295-300.

Fletcher, et al. "Quantifying Metabolic Asymmetry Modulo Structure in Alzheimer's Disease", Karssemeijer, et al. (Eds): IPMI 2007, LNCS 4584, pp. 446-457, 2007 ©Springer-Verlag Berlin Heidelberg 2007.

Kovalev, et al. "Asymmetry of Spect Perfusion Image Patterns as a Diagnostic Feature for Alzheimer'S Disease", Larson, et al. (Eds): MICCAI 2006, LNCS 4191, pp. 421-428, 2006 ©Springer-Verlag Berlin Heidelberg 2006.

Minoshima, et al. "A Diagnostic Approach in Alzheimer's Disease Using Three-Dimensional Stereotactic Surface Projections of Fluorine-18-FDG PET", Journal of Nuclear Medicine, V. 36, No. 7, Jul. 1995, pp. 1238-1248.

O'Mara, D., et al.; Measuring Bilateral Symmetry in Digital Images; 1996; IEEE Tencon. Digital Signal Processing Applications; vol. 1:151-156.

Olejarczyk, E., et al.; Comparison of Different Spect Images Analysis Methods for Inter-hemispheric Asymmetry Detection in Patients with Epileptic Symptoms; 2008; Biocybernetics and Biomedical Engineering; 28(4)33-41.

Zhou, et al. "Detection of Inter-Hemispheric Metabolic Asymmetries in FDG-PET Images Using Prior Anatomical Information", nEUROiMAGE 44 (2009) 35-42.

* cited by examiner

AUTOMATIC QUANTIFICATION OF ASYMMETRY

CROSS REFERENCE TO RELATED APPLICATIONS

This application is a national filing of PCT application Ser. No. PCT/IB2012/050025, filed Jan. 3, 2012, published as WO 2012/093353 A1 on Jul. 12, 2012, which claims the benefit of U.S. provisional application Ser. No. 61/429,777 filed Jan. 5, 2011, which is incorporated herein by reference.

The present application relates to the diagnostic arts. It finds particular application in conjunction with functional images of the brain, including but not limited to positron emission tomography (PET) images and single photon emission computed tomography (SPECT) perfusion images. However, it will be appreciated that the described technique may also find application with other medical imaging device systems, other anatomical regions, the examination of inanimate objects, or the like.

The human brain is mostly left-right symmetric, not only in terms of structure but also metabolism as measured by [18F] FDG PET imaging. Many subjects suffering from dementia also show symmetric impairment of brain metabolism. However, many dementia subjects exhibit asymmetric brain metabolism, in particular early in disease progression.

A determination of asymmetry in the brain has diagnostic value. With some forms of dementia, affected areas of the brain occur asymmetrically. For example, a high degree of asymmetry can be found in the very early stages of Alzheimer's disease. Measuring asymmetry can be used to detect or identify various types of dementia, including the early stages of Alzheimer's. Currently, a diagnostician manually compares sections of the brain or organ to determine how symmetric they are. This comparison calls for a great deal of skill and is difficult to quantize. Due to the subjective nature of the evaluations, comparing evaluations performed by different diagnosticians can be inaccurate. To further complicate a diagnosis, asymmetry in various regions of an organ, such as a brain, may be normal.

More specifically, one of the most effective ways of diagnosing the underlying disease causing dementia in its earlier stages is by performing an FDG-PET brain scan. Dementias like Alzheimer's disease cause typical patterns of hypometabolism in the brain. Unfortunately, accurate identification of these hypometabolic areas in FDG-PET brain scan images requires a great deal of skill, because these areas only show up as subtly different shades of gray. This is why reliable interpretation of FDG-PET brain scans is normally only performed by a highly experienced expert. In state-of-the-art analysis of FDG-PET images, asymmetry is often overlooked or not assessed, although it has diagnostic value. Slight asymmetries are hardly visible to the human eye.

Accordingly, there is a need for an automated quantification of asymmetry to aid a healthcare provider in a diagnosis.

The present application provides new and improved systems and methods, which overcome the above-referenced problems and others.

In accordance with one aspect, an apparatus, for detecting asymmetry in an object, comprises a processor programmed to perform the steps of comparing corresponding voxels on opposite sides of an image of the object. Based on the comparing, the apparatus generates at least one of an asymmetry map and an asymmetry index.

In accordance with another aspect, a method for detecting asymmetry comprises comparing pairs of corresponding pixels on opposite sides of an image of an object, and based on the comparing, generating at least one of an asymmetry map and an asymmetry index.

One advantage is that asymmetry can be more easily detected.

Another advantage is that asymmetry can be quantified.

Another advantage resides in detecting Alzheimer's disease at a very early stage.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

Figure 1:
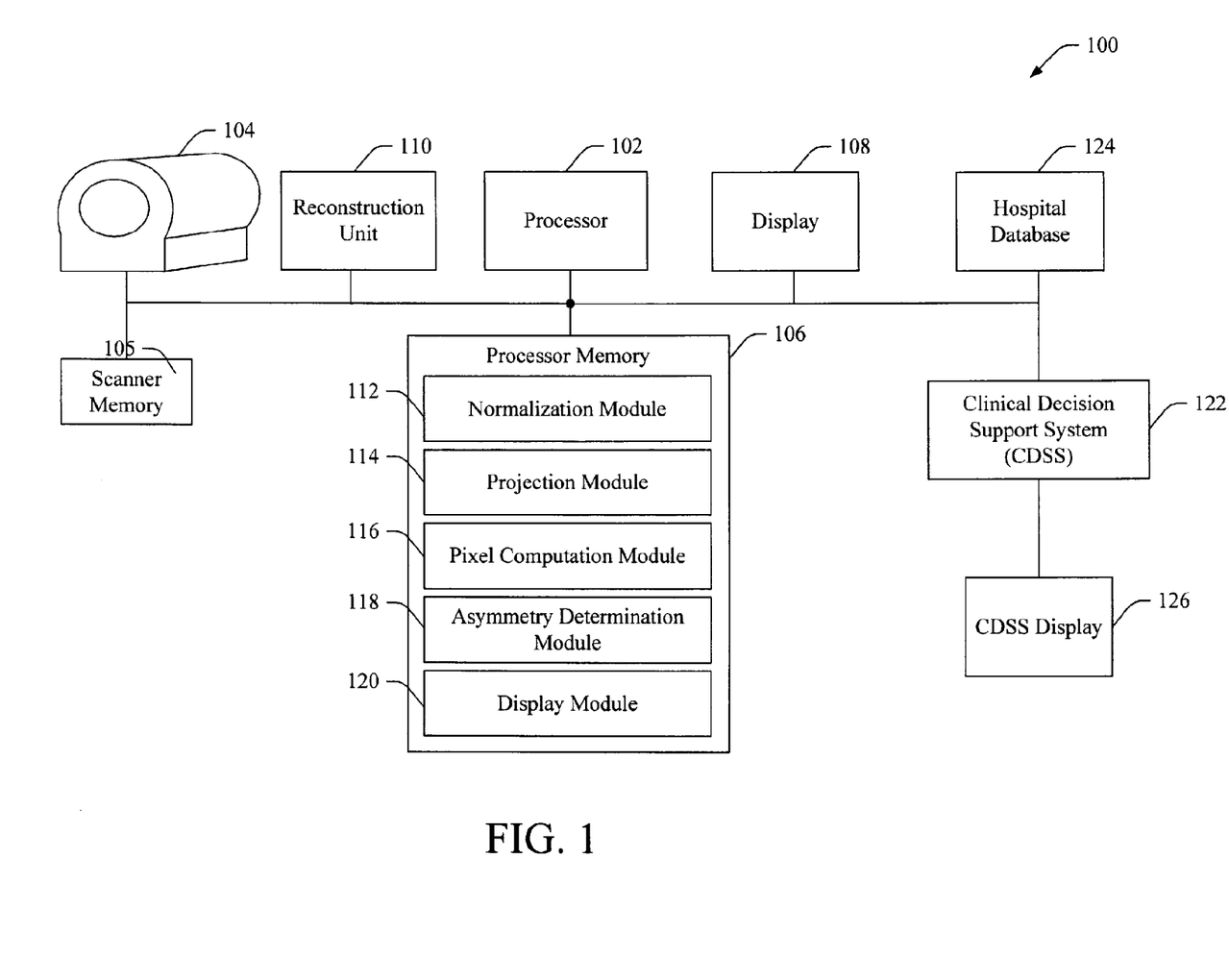
FIG. 1 illustrates a system that facilitates displaying an asymmetry map by comparing an acquired image to an existing template, in accordance with various aspects described herein.

FIG. 1 illustrates a system 100 that calculates an asymmetry index. The system 100 includes one or more processors 102 coupled to a functional scanner 104, such as a PET or other nuclear medicine scanner, and a scanner memory 105. In one embodiment, a processor memory 106 stores, and the processor 102 executes, computer-executable instructions for performing the various functions, methods, techniques, procedures, etc., described herein. The computer-executable instructions are stored as modules in the processor memory 106. In another embodiment, a series of engines, modules, hardware components or the like implement the below described functions. The system further includes a display 108 that presents information to a user.

The scanner 104 scans an object, such as a brain to generate functional image data, preferably in lists made with the received data time stamped. The image data is stored in the scanner memory 105.

A reconstruction unit 110 coupled to the scanner memory 105 accesses the image data and reconstructs the data into a three-dimensional image that represents the scanned object. In one embodiment, the image is reconstructed from PET using time-of-flight (TOF) information such that the three-dimensional image represents a distribution of a radiopharmaceutical in the brain or other organ. For example, if the radiopharmaceutical includes glucose, it is taken up into active regions of the brain with higher metabolic activity and little or no glucose is taken up into metabolically impaired or damaged regions. The impaired regions show up darker in the three-dimensional image.

A normalization module 112, in the form of hardware or a registration algorithm or instructions from the processor memory 106, fits the three-dimensional image to a standard brain atlas or template, e.g. a stereotactic normalization.

A projection module 114, in the form of a dedicated hardware or processor programmed to perform a projection algorithm or instructions, projects or maps the three-dimensional image of the brain, particularly the radiopharmaceutical distribution indicative of, up onto the brain surface. More specifically to the illustrated embodiments, the projection module maps the three dimensional image onto eight stereotactic surface projections, including left lateral, right lateral, superior, inferior, anterior, posterior left medial, and right medial. If the brain is symmetric, opposite sides of the brain, particularly opposite projection images, would be mirror image symmetric, i.e., corresponding pixels of the pair of projection images of opposite sides of the brain would be the same. The projection views are saved in the memory 106 and are selectively displayed on the display 108.

Lateral and medial projections of the left and right brain hemispheres have several advantages over volume images. This visual representation is easier to interpret. Surface projections reduce inter-subject as well as intra-subject variability caused by individual differences in cortical structure. Surface projections are therefore well suited to capture functional asymmetry (being more robust to structural asymmetry).

A pixel computation module 116 in the form of dedicated hardware or a processor programmed to perform a pixel computation algorithm or computer instructions, identifies corresponding, e.g. mirror image symmetric, pixels $x_i$ in each half of the brain e.g. the left and right sides. The pixel computation module 116 compares each pair of corresponding surface pixels to determine relative asymmetry. When a plurality of the stereotactic surface projections is used in the comparing, the duplicative information in two or more of the projection images is ignored, and the pixel computation module 116 does not assess duplicative values twice. Alternately, duplicative data can be eliminated during the mapping or projecting.

Figure 5:
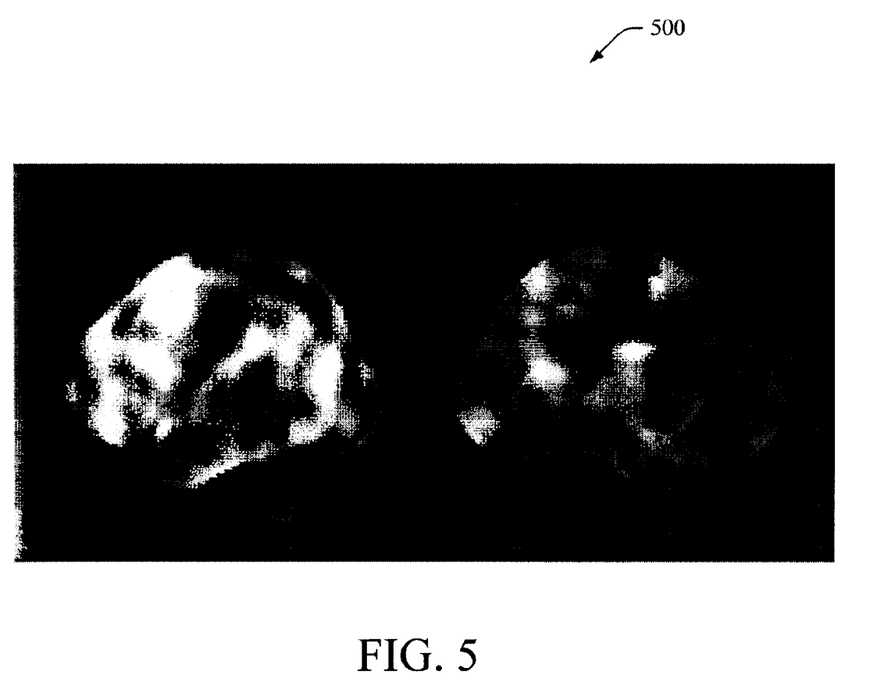
FIG. 5 illustrates an example asymmetry map.

An asymmetry determination module 118, in the form of hardware or a programmed processor, computes an asymmetry map, FIG. 5, or an asymmetry index value from the differences between corresponding pixels generated by the pixel computation module 116. In one embodiment, the system computes two asymmetry maps, including a medial plot and a lateral plot with intensity variations indicating relative degrees of asymmetry. In another embodiment, the system computes eight surface projections that also show intensity variations indicative of relative degrees of asymmetry.

In another embodiment, the asymmetry determination module 118 generates an asymmetry index. The asymmetry index is a numerical value that represents the relative asymmetry of the examined brain, as a whole or selected portions thereof, compared to a normal brain. In one embodiment, a scanned object that is relatively symmetric has a low asymmetry index. Whereas, a scanned object that is relatively asymmetric has a higher asymmetry index, e.g. number of standard deviations from normal. By providing the asymmetry index as a scalar representation, a user can quickly and efficiently determine the level of commonality between the scanned object and normal. A display module 120 converts outputs the asymmetry information (e.g. asymmetry map or index) to an appropriate format for display on the display 108.

In another embodiment, the asymmetry determination module 118 outputs the asymmetry index to a clinical decision support system (CDSS) 122. The CDSS 122 can take into account a variety of factors (e.g. age, other test results, etc.) to provide a more complete and accurate diagnosis or suggested treatment plan. The CDSS 122 is operatively connected to a hospital database 124, which acts as a repository for patient information. The information may include, but is not limited to information relating a specific patient for whom the asymmetry index corresponds. For example, the hospital database 124 can include information relating to the patient's age, demographics, prior medical history, etc. The CDSS 122 can retrieve information (e.g. results of other tests of a patient) from the hospital database 124, and use the retrieved information in conjunction with the asymmetry index to generate probabilities of various diagnoses or proposed courses of treatment. The CDSS 122 can also mitigate the need for a visual interpretation of the asymmetry by a physician, since the asymmetry index can be automatically machine determined. The system can aid less-experienced physicians in obtaining an accurate diagnosis. The CDSS 122 can output the generated results to the CDSS display 126 for presentation.

Figure 2:
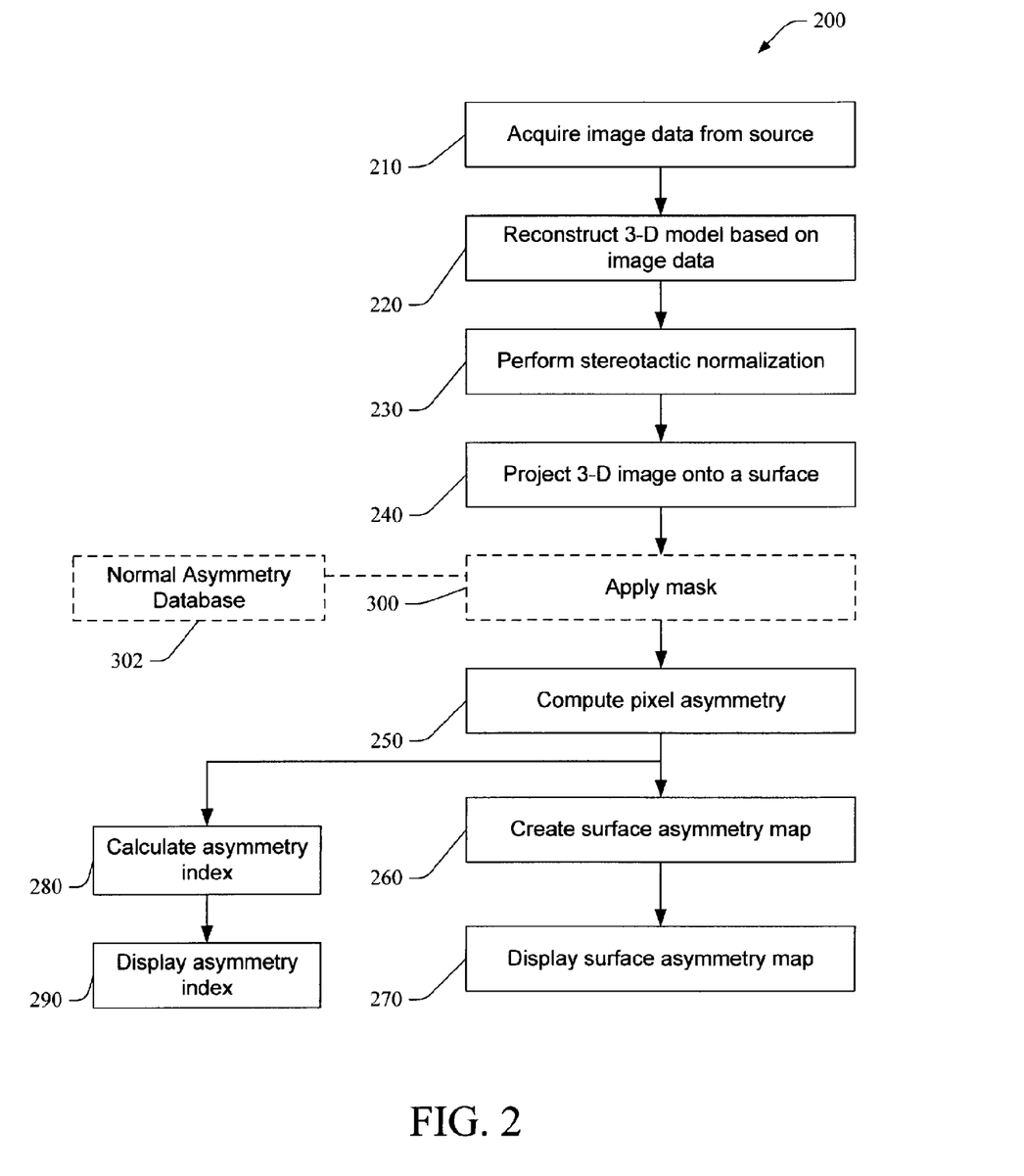
FIG. 2 illustrates an asymmetry map calculation sequence that displays an asymmetry map and a corresponding asymmetry index, which eliminates the need for manual comparison of images to determine asymmetry or abnormalities.

FIG. 2 illustrates a method 200 for calculating asymmetry information, in accordance with various features. While the method is described as a series of acts, it will be understood that not all acts may be required to achieve the described goals and/or outcomes, and that some acts may, in accordance with certain aspects, be performed in an order different that the specific orders described. The acts can be performed by suitably programmed processors, such as 102 and 110.

At 210, an object, e.g. brain, is scanned to generate image data associated with the object. For metabolic brain imaging, PET imaging is advantageous, and perfusion SPECT imaging is also useful. At 220, the image data is reconstructed to form a three-dimensional image of the scanned object. At 230, a stereotactic normalization is performed on each voxel of the reconstructed three-dimensional image. The voxels of the reconstructed three-dimensional image are spatially transformed to standard coordinates, such as a symmetrical brain atlas or template, e.g. using a non-affine image registration. In this manner, the size and shape of the brain is standardized for all patients. At 240, the three-dimensional image is mapped, e.g. projected, to a series of two-dimensional images projected onto the brain surface. The two-dimensional images can comprise a multitude of views of each hemisphere, including left lateral, right lateral, superior, inferior, anterior, posterior, left medial, and right medial, among others.

At 250, corresponding pairs of pixels of the surface projections of the left and right side of the brain are compared to a normative asymmetry map for similarity. A database stores the normative asymmetry maps, which can represent normal brains. Various ways of computing the asymmetry from the corresponding pixel pairs are described below.

At 260, a brain surface asymmetry map is created from the differences or relative asymmetry between the corresponding left-right pixel pairs. For example, the surface asymmetry map shows relative asymmetry by color/grey scale coding of a medial and lateral projection of one side of the brain (the other side would look the same but mirror image reversed). Relative differences in the corresponding pixel pairs are represented by color or grey scale shading differences within the asymmetry map. For example, lighter shades can indicate surface portions that are more asymmetric. At 270, projections of the surface asymmetry map, such as the medial and lateral projections, are displayed to a user on display 108 or any other suitable display device.

At 280, an overall asymmetry value, such as a scalar asymmetry index, is calculated. The asymmetry index represents a level of asymmetry of the overall or some selected portion of the brain. The asymmetry index can be represented as a scalar number that summarizes the level of asymmetry over the scanned object. In one embodiment, the asymmetry index is computed using a mean of the asymmetry level of each pixel on the map. For example, the asymmetry of each pixel can be ranked on a scale from 1 to 10. The mean asymmetry level of the pixels on the asymmetry map can be subsequently computed. Similarly, the system and method can compute an asymmetry index that represents a median asymmetry of the pixels in a similar way. In another embodiment, the overall asymmetry measure is a vector of multiple scalar asymmetry indices, each index derived with a different method at 250.

The calculated asymmetry index, or a vector of multiple scalar asymmetry indices, is optionally sent to a clinical decision support system (CDSS) to assist with a diagnosis. The CDSS can use the asymmetry index in conjunction with other image-based information (e.g. volume of hypometabolism) or non-image-based information (age, lab tests, etc.) to provide information relating to the patient. Decision support software aims to assist in the interpretation of the images to the point where accurate diagnoses can be made by less experienced physicians. This could make diagnostic services for the early diagnosis of dementia much more widely available. The automatic assessment of brain asymmetry is a useful marker of brain non-normality in general, and early dementia in particular.

As stated above, the system 100 includes the processor 104 that executes, and the processor memory 106, which stores, computer-executable instructions (e.g., routines, programs, algorithms, software code, etc.) for performing the various functions, methods, procedures, etc., described herein. Additionally, "module," as used herein, denotes a set of computer-executable instructions, software code, program, routine, ASICs, array processors and other hardware components, or the like, as will be understood by those of skill in the art.

The memory may be a computer-readable medium on which a control program is stored, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor can read and execute. In this context, the systems described herein may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

Figure 3:
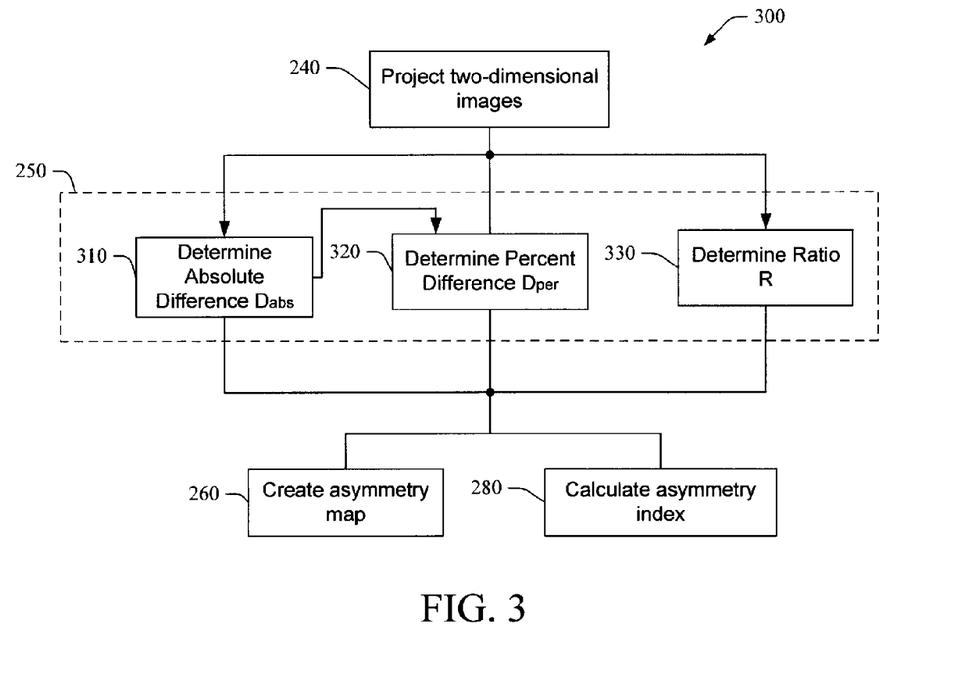
FIG. 3 illustrates the use of a mask in calculation of an asymmetry index.

In one embodiment, pixels of the two-dimensional images of the object are masked before computing the asymmetry. An object may be expected to be asymmetric in some areas, while symmetric in others. Some portions are asymmetric in normal brains. A mask is applied at 300 to exclude pixels from the calculation which are expected, under normal circumstances, to exhibit asymmetry. Alternatively, the applied mask excludes pixels with low reliability. For example, the mask can exclude pixels with a standard deviation of the asymmetry index above a certain threshold in a group of normal brains stored in a normal asymmetry database 302.

With reference to FIG. 3, the asymmetry at each corresponding pixel pair $x_{Li}$, $x_{Ri}$ in the left and right hemispheres is calculated. In one embodiment, at 310 the absolute difference ($D_{abs}$) for each pixel pair is calculated by determining the absolute value of the difference between the corresponding left and right pixels ($x_{Li}$, $x_{Ri}$), i.e., $D_{abs}(x_i)=|x_{Li}-x_{Ri}|$. In another embodiment, a percent difference $D_{per}$ is determined at 320, i.e. $D_{per}(x_i)=2*D_{abs}(x_i)/(x_{Li}+x_{Ri})$. In another embodiment, at 330 the method determines a ratio $R(x_i)$ of the corresponding left and right pixels $x_{Li}$, $x_{Ri}$ i.e.:

$$R(x_i)=(x_{Li}/x_{Ri})-1.$$

The absolute difference, the relative (percent) difference, or the ratio can be used in step 260 to calculate the asymmetry map. The grey scale or color values are set in accordance with the magnitude of the difference, percent difference or ratio. To calculate the aggregate asymmetry index in step 280, the absolute values of asymmetry pixel values are considered (i.e. $D_{abs}$, $|D_{per}|$, $|R|$). In one embodiment, a statistical property, such as a mean or median or a percentile of the asymmetry values, is computed. In another embodiment, a threshold is chosen, e.g. a percent difference of 10% for $D_{per}$ and the number of pixels with $D_{per}$ greater than the threshold value is counted.

Figure 4:
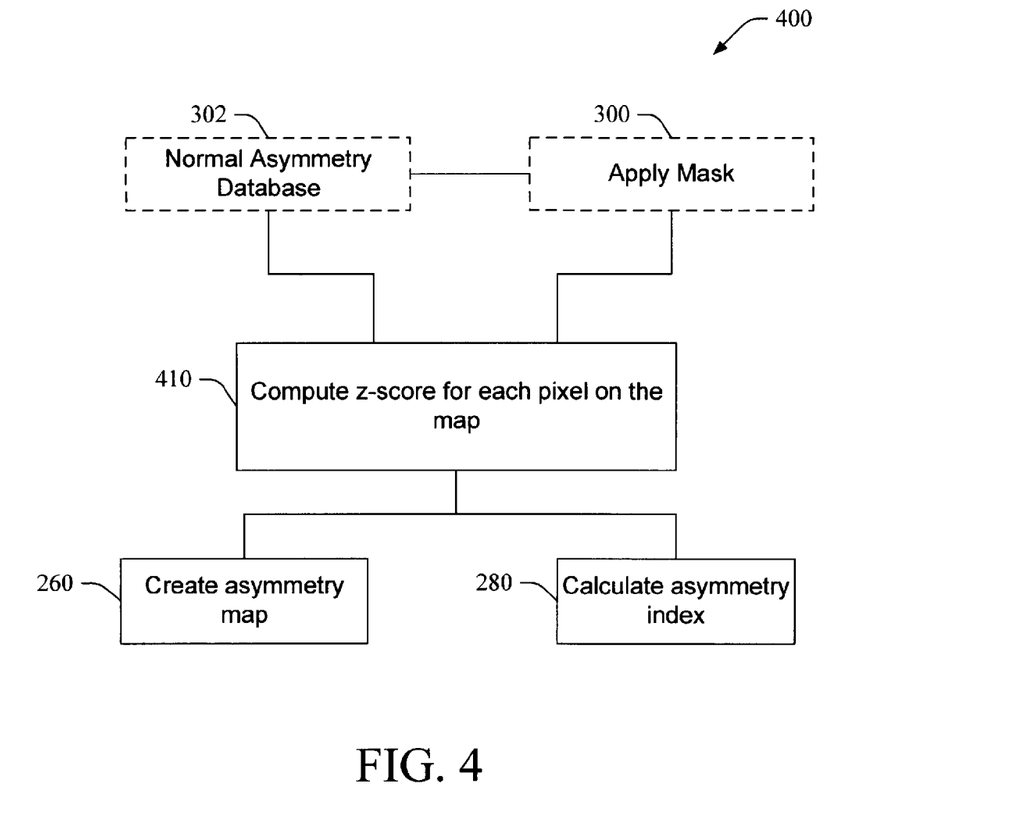
FIG. 4 illustrates the use of a z-score in calculation of an asymmetry index.

FIG. 4 illustrates another calculation of asymmetry information by mapping a z-score before computing an asymmetry index. Before computing an asymmetry index, the method computes a z-score for each corresponding left-right pixel pair on the two-dimensional map. For example, the following formula can be employed to calculate the z-score for each pixel $x_i$: $z(x_i)=(a(x_i)-\text{mean\_a}(x_i))/\text{std\_a}(x_i)$, where $a(x_i)$ represents the asymmetry measure, such as difference, percent difference, ratio, or the like, at the pixel $x_i$. Mean_a( ) and std_a( ) represent mean and standard deviation of the asymmetry measure a( ) previously computed on a database of normal brain images. At 260, the asymmetry map is generated using the z-score to set the grey scale or color value at the corresponding pixel. At 280, the z-score is used to compute the asymmetry index.

FIG. 5 illustrates an example asymmetry map generated by the system 100 and the method 200. The map shows a lateral and medial plot of relative intensity differences. Pixels are shown in different shades based on asymmetry values of the corresponding voxels. Bright pixels denote pixels where image intensity is larger in the right hemisphere; dark pixels are associated with higher image intensity in left hemisphere.

Figure 6:
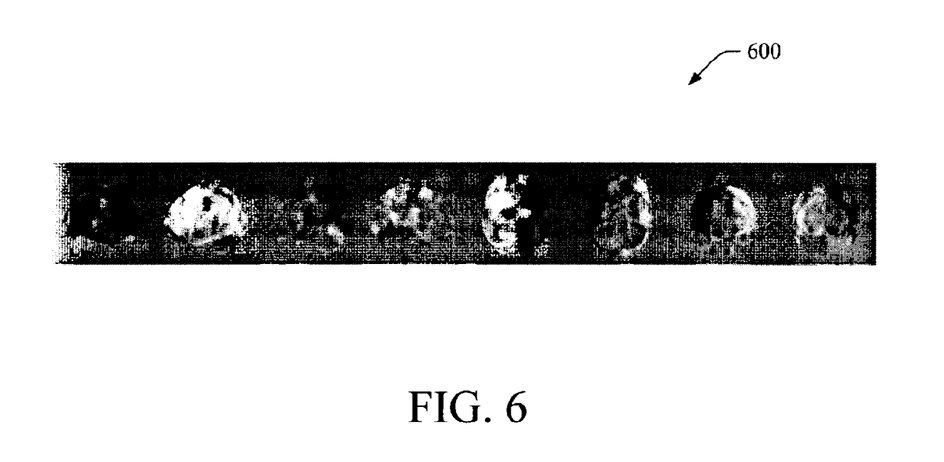
FIG. 6 illustrates another example asymmetry map.

FIG. 6 illustrates an example asymmetry map generated by the system 100 and the method 200. The map shows two-dimensional images, including left lateral, right lateral, superior, inferior, anterior, posterior, left medial, and right medial, but is not limited to such images. Pixels are shown in different shades based on asymmetry values of the corresponding voxels. Bright pixels denote pixels where image asymmetry is larger; dark pixels are associated with more symmetric pixels.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. An apparatus for detecting asymmetry in an object, the apparatus comprising:
   a processor programmed to:
     fit a three-dimensional image of the object to a preselected shape,
     project the three-dimensional image of the object fit to the predetermined shape onto a two-dimensional surface image;
     compare corresponding voxels on opposite sides of an image of the object;
   based on the comparing, generating an asymmetry index by performing the steps of:
     determining an asymmetry level of each pair of compared pixels, determining a scalar value corresponding to a mean or median of the asymmetry values of the compared pixels, the scalar value being the asymmetry index.

2. The apparatus according to claim 1, wherein the object is a brain and the processor is further programmed to:
fit a three-dimensional image of the brain to a standard brain atlas.

3. The apparatus according to claim 1, wherein the processor is further programmed to:
calculate a plurality of the scalar value asymmetry indices with each of a plurality of methods;
control a display to display the plurality of calculated scalar value asymmetry indices as a vector.

4. The apparatus according to claim 3, wherein the processor is further programmed to calculate the scalar value asymmetry indices by:
computing an absolute difference between corresponding pairs of pixels on opposite sides of the surface image and determining a mean or median of the absolute differences as the asymmetry index;
computing a relative difference between corresponding pairs of pixels on opposite sides of the surface image and determining a mean or median of the relative differences as the asymmetry index;
computing a ratio between amplitudes of corresponding pixel pairs on opposite sides of the surface image and determining a mean or median of the ratios as the asymmetry index.

5. The apparatus according to claim 1, wherein the processor is further programmed to:
compute the scalar value based on how much the pixels in each compared corresponding pixel pair differ and a number of the compared corresponding pixel pairs which differ by more than a threshold or percentage.

6. The apparatus according to claim 2, wherein the processor is further programmed to:
apply a mask to exclude corresponding pairs of pixels of the surface image which are normally asymmetric in a normal brain, wherein applying the mask is performed after the projecting and before the comparing step.

7. The apparatus according to claim 1, further including:
a hospital database which stores patient data including patient age, demographics, medical history, and test results;
a clinical decision support system which receives and uses the patient data retrieved from the patient database and the at least one of the asymmetry map and asymmetry index to calculate probabilities of each of a plurality of potential diagnoses.

8. A method for detecting asymmetry, the method comprising:
fitting a three-dimensional image of an object to a preselected shape,
projecting the three-dimensional image of the object fit to the predetermined shape onto a two-dimensional surface image;
comparing pairs of corresponding pixels on opposite sides of the surface image of an object;
based on the comparing, generating a scalar asymmetry value by at least one of:
computing an absolute difference between the corresponding pairs of pixels on opposite sides of the surface image and determining a mean or median of the absolute differences as the asymmetry value;
computing a relative difference between the corresponding pairs of pixels on opposite sides of the surface image and determining a mean or median of the relative differences as the asymmetry value;
computing a ratio between amplitudes of the corresponding pixel pairs on opposite sides of the surface image and determining a mean or median of the ratios as the asymmetry value.

9. The method according to claim 8, further including:
before the projecting step, mapping the three-dimensional image of the object to a preselected shape or atlas.

10. A method of generating a scalar asymmetry index comprising:
receiving a 3D image of a brain of a patient;
mapping the 3D brain image to a preselected shape or brain atlas which is symmetric about a medial plane and has a surface;
projecting voxels of the 3D brain image onto the surface to create a 2D surface image with corresponding pairs of pixels on opposite sides of the medial plane;
comparing the pixels of each corresponding pair of pixels to determine whether the pixels of each corresponding pair of pixels deviate from each other;
based on the comparing, generating an asymmetry index by performing the steps of:
determining an asymmetry level of each pair of compared pixels,
determining a scalar value corresponding to a mean or median of the asymmetry values of the compared pixels, the scalar value being the asymmetry index.

11. The method according to claim 10, wherein the comparing step includes determining at least one of:
an absolute difference between pixels of each corresponding pixel pair,
a relative difference between pixels of each corresponding pixel pair, and
a ratio between pixels of each corresponding pixel pair.

12. The method according to claim 10, further including:
determining a degree to which each deviating pixel pair deviates and where the scalar numerical value is calculated based on the relative number or percent of pixel pairs that are determined to deviate and the determined degrees to which the deviating pixel pairs deviate.

13. The method according to claim 8, further including:
retrieving patient data of the patient including at least patient age, medical history, and test results from a hospital database;
generating a treatment plan based on the patient data and the scalar asymmetry value.

14. A system for detecting brain maladies at an early development stage, the system comprising:
a hospital database which stores patient medical and demographic data;
a processor programmed to perform the steps of:
projecting voxels of a 3D brain image onto one or more 2D surfaces,
comparing corresponding voxels on opposite sides of the projected 2D brain image,
based on the comparing, generating an asymmetry index by performing the steps of:
determining an asymmetry level of each pair of compared pixels,
determining a scalar value corresponding to a mean or median of the asymmetry values of the compared pixels, the scalar value being the asymmetry index; and
a clinical decision support system (CDSS) that generates at least one of a proposed diagnosis or treatment plan from the asymmetry index or map and the patient medical and demographic data from the hospital database.

15. An apparatus for detecting asymmetry in a brain, the apparatus comprising:
a processor programmed to:
fit a three-dimensional image of the brain to a brain atlas,
project the three-dimensional image of the brain fit to the brain atlas onto a two-dimensional surface image;
apply a mask which excludes corresponding pixel pairs on opposite sides of the surface image of the brain with a standard deviation above a threshold in normal brains;
compare non-excluded corresponding pixels on opposite sides of the surface image of the brain;
based on the comparing, generating at least one of an asymmetry map and an asymmetry index.

16. The system according to claim 14, wherein the clinical decision support system determines from the medical and demographic data and the symmetry index a probability that the patient is inflicted with each of a plurality of diagnoses.

17. The system according to claim 14, wherein the hospital database stores test results and medical history and wherein the clinical decision support system generates a suggested treatment plan based on the medical history, the test results, and the asymmetry index.

* * * * *